United States Patent
Bush et al.

(10) Patent No.: US 10,314,934 B2
(45) Date of Patent: Jun. 11, 2019

(54) SYSTEM AND METHOD FOR DISPENSING MATERIAL

(71) Applicant: The Procter & Gamble Company, Cincinnati, OH (US)

(72) Inventors: Stephan Gary Bush, Liberty Township, OH (US); Faiz Feisal Sherman, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/632,509

(22) Filed: Jun. 26, 2017

(65) Prior Publication Data

US 2018/0369443 A1  Dec. 27, 2018

(51) Int. Cl.
| | |
|---|---|
| A61L 9/14 | (2006.01) |
| A61L 9/03 | (2006.01) |
| B01F 3/04 | (2006.01) |
| B05B 12/04 | (2006.01) |
| B05B 17/06 | (2006.01) |
| B41J 2/175 | (2006.01) |

(52) U.S. Cl.
CPC ...... *A61L 9/14* (2013.01); *A61L 9/03* (2013.01); *B01F 3/04* (2013.01); *B05B 12/04* (2013.01); *A61L 2209/11* (2013.01); *A61L 2209/132* (2013.01); *B05B 17/0615* (2013.01); *B05B 17/0669* (2013.01); *B41J 2/17513* (2013.01)

(58) Field of Classification Search
CPC ...... A61L 9/145; A61L 9/03; A61L 2209/132; A61L 2209/11; B41J 2/17513; B05B 17/0669; B05B 17/0615; B05B 17/0646; B05B 17/0684; B01F 3/04; B01F 3/04007; B01F 3/04085; B01F 3/04014
See application file for complete search history.

(56) References Cited

U.S. PATENT DOCUMENTS

| | | |
|---|---|---|
| 9,592,666 B2 | 3/2017 | Bush et al. |
| 9,616,447 B2 | 4/2017 | Bush et al. |
| 2002/0054197 A1 | 5/2002 | Okada et al. |
| 2004/0028551 A1 | 2/2004 | Kvietok |
| 2008/0085511 A1 | 4/2008 | Peck |
| 2015/0290670 A1 | 10/2015 | Bush et al. |
| 2015/0367356 A1* | 12/2015 | Gruenbacher ........ B05B 1/24 239/135 |
| 2016/0271639 A1 | 9/2016 | Bush et al. |

FOREIGN PATENT DOCUMENTS

WO    WO2017200993 A1    11/2017

OTHER PUBLICATIONS

Search Report; PCT/US2018/039381; dated Oct. 30, 2018; 15 Pages.

* cited by examiner

*Primary Examiner* — Geoffrey S Mruk
(74) *Attorney, Agent, or Firm* — Abbey A. Lopez

(57) ABSTRACT

A fluid dispensing method, the method comprising steps of: providing a drop on demand apparatus comprising a plurality of nozzles in fluid communication with a fluid reservoir; selecting a subset of the plurality; dispensing fluid via the selected subset of the plurality; pausing all dispensing of fluid; selecting a second subset of the plurality; dispensing fluid via the second selected subset of the plurality.

10 Claims, 2 Drawing Sheets

SYSTEM AND METHOD FOR DISPENSING MATERIAL

FIELD OF THE INVENTION

The invention relates to systems and method for dispensing materials. The invention relates particularly to systems and method for dispensing materials by using a thermal jetting system.

BACKGROUND OF THE INVENTION

Dispensing materials via the heating of a volatile carrier to form a transport jet is well known. Thermal ink-jet systems provide a means for the creation and precise deposition of ink droplets upon a substrate. Thermal driven systems may also be used to drive the dispensing or dispersion of other materials, again by volatilizing a carrier or the actual material to be dispensed.

The 'atomization' of volatile oils to disperse them in an environment for the purpose of spreading a fragrance in the environment is also known. Typical dispersion systems create a set of oil droplets which disperse in the environment. Under-performing dispensing nozzles may degrade the dispensing performance of the system in that that particular nozzles no longer dispense completely, or in some instances at all. This may reduce the ability of the system to effectively dispense fluid as desired.

What is needed is an improved system and method for the dispersion of materials into an environment such that the material may be easily dispersed in the environment while reducing the degradation of nozzle performance and reducing the operational effect of under-performing nozzles.

SUMMARY OF THE INVENTION

In one aspect, a fluid dispensing method comprises the steps of: providing a drop on demand apparatus comprising a plurality of nozzles in fluid communication with a fluid reservoir; selecting a subset of the plurality; dispensing fluid via the selected subset of the plurality; pausing all dispensing of fluid; selecting a second subset of the plurality; dispensing fluid via the second selected subset of the plurality.

DETAILED DESCRIPTION OF THE INVENTION

Figure 1:
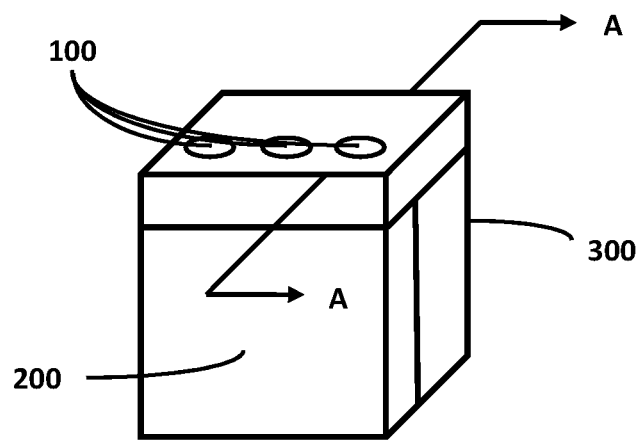
FIG. 1 provides a schematic representation of an embodiment of the invention.

The present disclosure is directed to a fluid delivery system configured to eject a working fluid from a thermal or piezo-electric micro-fluidic die. The die includes one or more activating elements formed in a substrate. The activating elements may be either thermal or piezo-electric. The substrate may be covered by a dielectric layer, shielding the activating elements from direct contact with the working fluid intended for ejection by the system. Each activating element is disposed adjacent to a fluid chamber and in turn to a nozzle disposed adjacent to the fluid chamber. Well known structures associated with electronic components and the details of semiconductor fabrication have not been included in the description.

The working fluid may comprise a solvent and a solubilized active agent. Solvents include water, alcohol, and other fluids which may be readily volatilized using either heat or ultrasonic energy sources. In one embodiment, the active agent comprises a fragrance agent. The fragrance agent may comprise one or more fragrance elements such that the overall agent may yield a complex fragrance comprising a plurality of fragrance notes in combination.

In one aspect, the invention comprises an apparatus for dispensing a liquid into an environment. The apparatus comprises a reservoir containing the liquid. The reservoir is in fluid communication with a dispensing element or print head. The connection between the reservoir and the dispensing element enables the fluid to flow from the reservoir to flow into chambers of the dispensing element. The apparatus die further comprises a plurality of nozzles from which fluid is dispensed. For each dispensing cycle, the activating element of a subset of the total number of nozzles are energized resulting in an attempt to dispense fluid from the respective nozzles. The subset may be as few as one nozzle or as many as all the available nozzles. The subset may be pre-defined as particular nozzles of the total number of nozzles, or the subset may be selected using a random number function to select numbered nozzles within the total number of nozzles up to a predefined or randomly selected quantity of nozzles has been selected.

The size of the respective subsets may be chosen randomly or according to the desired volume to be dispensed. In one embodiment, each subset is selected such that the total volume of fluid dispensed from the number of nozzles is at least approximately equal to a predefined desired fluid volume. The selection of the desired volume may take into consideration the ejection efficiency of the nozzle configuration as well as the firing rate of the nozzles with respect to the refill time of the fluid chambers serving the nozzles as well as allowing for a percentage of the nozzles to have failed or otherwise be underperforming. In this way, the firing of the respective subsets will be more likely to result in the actual dispensing of the desired quantity of fluid from the apparatus.

Once selected, the chosen or defined nozzles are fired by energizing the activation element. The firing results in a dispensing event where the desired quantity of fluid is dispensed from the apparatus via the selected nozzles. The apparatus is paused between dispensing events. Subsequent to the pause of the apparatus, a second subset is fired for the next event. The second subset may also be pre-defined or randomly selected as set forth above. Predefined subsets may be selected such that there is no overlap between subsets. This selection enables the subset to be energized in sequence resulting in a firing pattern wherein no subset of nozzles is fired again until after each other subset of nozzles has been fired in the intervening time interval. As an example, a die may comprise 80 nozzles subdivided into four subsets, nozzles: 1-20, 21-40, 41-60, and 61-80. Nozzles 1-20 may be fired, followed by the firing of nozzles 21-40, then 41-60 and then 61-80, then returning to nozzles 1-21.

The firing order of the respective subsets may be fixed or randomized. For random firing sequences, the randomization may be with or without consideration of the previous firing order. IN other words, the random firing order may take into account the previous firing order to ensure that no nozzles subset is fired again until all other subsets have been fired, or the randomization may proceed without consideration of this information.

The duration of the firing events and pauses may be similar of different. In one embodiment, the duration of the pause is substantially greater than the duration of the firing event.

In one example configuration, a thermal inkjet die having 80 nozzles is coupled to a reservoir with approximately 20 mL capacity. The liquid to be dispensed is a fragrance composition comprising 95% perfume oil mixture and 5% propylene glycol (propane-1,2-diol), with the composition having a specific gravity of 0.85. The volume ejected with each activation of an inkjet heater is approximately 11 pL. The desired dispense rate over time is 60 mg/hr. The desired firing frequency, chosen to maximize the projection of droplets into the living space, is 3000 Hz. The electrical pulse required to activate an individual thermal inkjet heater is 2.5 μs, with a 2 μs pause between successive heater activations. The nozzles of the inkjet die are individually addressable, a configuration which is chosen in part to minimize the size and current supply capacity of the power supply.

In the above configuration, it is not possible to fire all nozzles in the inkjet array in sequence at the desired firing frequency due to the number of nozzles, their required firing pulse timing, and the time available at a 3000 Hz repetition rate. Instead, in one configuration, a subset of 20 nozzles is fired repeatedly at 3000 Hz for 0.5 s, followed by a 9.5 s idle period. In the next burst, a different subset of 20 nozzles is fired. This configuration provides simplicity in the control algorithm, since the sequence of nozzles does not have to be reconfigured by the firmware during the burst event, but rather can be reconfigured during the idle period. Rotation of the subset of nozzles among the entire array from burst to burst ensures that, in the event there are a small number of defective nozzles in the array, the desired 60 mg/hr dispense rate is not significantly reduced. In this configuration, the subsets of 20 nozzles are selected as adjacent groups, so that the momentum of the stream of droplets, and thus the projected of the drops into the living environment, is maximized.

In this configuration, the pulse timing, the nozzle sequencing, and the firing timing are determined by firmware running on a microcontroller, an ST Microelectronics STM32L476ZG. In one embodiment, the system may comprise a plurality of fluid reservoirs containing either identical or dissimilar fluids. Each reservoir is in fluid communication with a dispensing die comprising a plurality of nozzles grouped into sets of nozzles as described above. Either a single common die or independent dies for each reservoir may be used. At least a portion of the nozzles may be operated in the manner set forth in the method, taking into consideration the volume of fluid considered necessary or desirable for each dispensing cycle.

As illustrated in FIG. 1, the device 1000, comprises a plurality of dispensing elements 100, a fluid reservoir 300 in communication with the dispensing elements, and a control element 200 in electrical communication with the dispensing elements.

Figure 2:
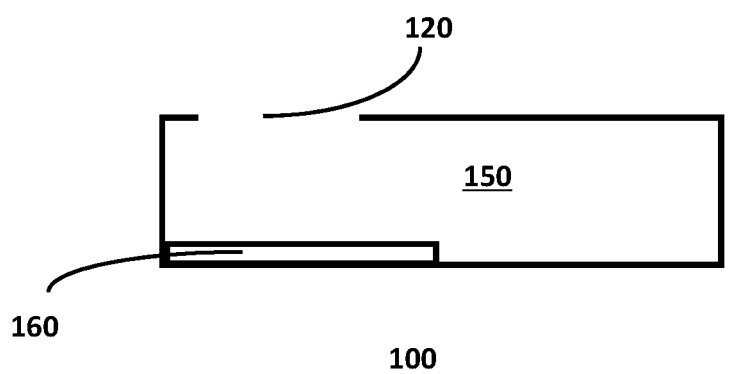
FIG. 2 provides a schematic sectional representation of a chamber of an embodiment of the invention, taken along section line AA of FIG. 1.

FIG. 2 provides a sectional view of a portion of FIG. 1 taken along line AA, showing the interior structure of a dispensing element 100 having a chamber 150, a nozzle, 120 and an activation element 160.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for dispensing a fluid, the method comprising steps of:
   a) providing a drop on demand apparatus comprising a plurality of nozzles in fluid communication with a fluid reservoir;
   b) selecting a subset of the plurality;
   c) repeatedly dispensing fluid via the selected subset of the plurality in a first burst;
   d) pausing all dispensing of fluid;
   e) selecting a second subset of the plurality;
   f) repeatedly dispensing fluid via the second selected subset of the plurality in a second burst.

2. The method according to claim 1 wherein the step of: providing a drop on demand apparatus comprising a plurality of nozzles in fluid communication with a fluid reservoir, comprises providing a thermal drop on demand apparatus.

3. The method according to claim 1 further comprising steps of:
   g) selecting a multitude of non-overlapping subsets of the plurality;
   h) alternating the dispensing of fluid via one of the multitude of subsets and pausing wherein for any first subset of the multitude to dispense fluid, each other subset of the multitude dispenses fluid prior to the first subset again dispensing fluid.

4. The method according to claim 1 wherein the step of providing a drop on demand apparatus comprising a plurality of nozzles in fluid communication with a fluid reservoir, comprises providing a fluid comprising a fragrance composition.

5. The method according to claim 1 wherein the first subset of the plurality of nozzles is selected randomly.

6. The method according to claim 1 wherein the steps of dispensing fluid each yield a similar volume of fluid output.

7. The method according to claim 1 wherein the time associated with each fluid dispensing step is substantially less than the time associated with the pausing of dispensing.

8. The method according to claim 1 wherein the step of: providing a drop on demand apparatus comprising a plurality of nozzles in fluid communication with a fluid reservoir, comprises providing a drop on demand apparatus comprising a plurality of nozzle sets, each nozzle set in fluid communication with one reservoir of a plurality of fluid reservoirs.

9. The method according to claim 1 wherein the step of: providing a drop on demand apparatus comprising a plurality of nozzles in fluid communication with a fluid reservoir, wherein the apparatus comprises about 80 dispensing nozzles, comprises providing a drop on demand apparatus comprising a plurality of nozzle sets, each nozzle set in fluid communication with one reservoir of a plurality of fluid reservoirs, each nozzle set comprising about 80 nozzles.

10. The method according to claim 1, wherein no subset of the plurality is fired again until each other subset of the plurality is fired.

* * * * *